(12) United States Patent
Trewhella et al.

(10) Patent No.: US 7,723,065 B2
(45) Date of Patent: May 25, 2010

(54) CONDITIONS FOR REACTIONS MEDIATED BY YEAST

(75) Inventors: Maurice Arthur Trewhella, Hoppers Crossing (AU); Nick Athanasiou, Yarraville (AU); Andrew John Smallridge, Hampton East (AU)

(73) Assignee: Victoria University, Victoria (AU)

( * ) Notice: Subject to any disclaimer, the term of this patent is extended or adjusted under 35 U.S.C. 154(b) by 933 days.

(21) Appl. No.: 10/814,891

(22) Filed: Mar. 31, 2004

(65) Prior Publication Data

US 2005/0084943 A1   Apr. 21, 2005

(30) Foreign Application Priority Data

Oct. 16, 2003   (AU)   ............................... 2003905675

(51) Int. Cl.
 *C12P 1/02*   (2006.01)
(52) U.S. Cl. .................. 435/41; 435/128; 435/130; 435/132; 435/166; 435/171
(58) Field of Classification Search ...................... None
 See application file for complete search history.

(56) References Cited

OTHER PUBLICATIONS

Howarth J, James P, Dai J, Immobilized baker's yeast reduction of ketones in an ionic liquid, [bmim]PF6 and water mix, Tetrahedron Letters, 2001, 42: 7517-7519.*

Kumar A, Ner DH, Dike SY, A New Chemoenzymatic Enantioselective Synthesis of R-(−)-Tomoxetine, R- and S-Fluoxetine, Tetrahedron Letters, 1991, 32(16): 1901-1904.*

Liu X, Zhu T-S, Sun P-D, Xu J-H, Asymmetric Reduction of Aromatic Ketones by the Baker's Yeast in Organic Solvent Systems, Synthetic Communications, 2001, 31(10): 1521-1526.*

Chem 231 Lecture No. 10 Sp 1999.*

Ohta et al. "Asymmeteric Reduction of Nitro Olefins by Fermmenting Baker's Yeast." J. Org. Chem. vol. 54, pp. 1802-1804. 1989.*

Kawai et al. "Asymmeteric Reduction of nitroalkenes with baker's yeast." Tetrahedron: Asymmetry. vol. 12, pp. 309-318. 2001.*

Y. Gao and K. B. Sharpless—"Asymmetric Synthesis of Both Enantionmers of Tomoxentine and Fluoxentine. Selective Reduction of 2, 3-Epoxycinnamyl Alcohol with Red-A1", J. Org. Chem. 1988, 53, 4081-4084. © 1988 American Chemical Society.

Badan S. Deol et al., Asymmetric Reduction of Carbonyl Compounds by Yeast. II; Aust. J. Chem., 1976, 29, 2459-67, 9 pages.

* cited by examiner

*Primary Examiner*—Anish Gupta
(74) *Attorney, Agent, or Firm*—Brooks Kushman P.C.

(57) ABSTRACT

Organic compounds, such as precursors for aryl ethylamines such as ephedrine, aryl propylamines such as fluoxetine and propionic acid derivatives such as ibuprofen, naproxen and fenoprofen, are subjected to a yeast mediated reduction conducted in the absence of a solvent. The yeast is moistened with water and contacted with the organic compound. The yeast may then be contacted with an organic solvent to dissolve the product of the reaction into the solvent, and a solid/liquid separation used to separate the product from the yeast.

20 Claims, No Drawings

CONDITIONS FOR REACTIONS MEDIATED BY YEAST

BACKGROUND OF THE INVENTION

1. Field of the Invention

The present invention relates to new environments in which to conduct certain classes of chemical reactions. The present invention particularly relates to new methods and environments for the synthesis of useful pharmaceutical compounds such as aryloxy phenyl propylamines (e.g. Prozac; Trade Mark of Eli Lilly, Inc.), 2-aryl ethylamines (eg ephedrine) and propionic acid derivatives (eg. ibuprofen).

2. Background Art

Due to the complex molecular structure of many organic compounds which have pharmacological activity, it is common for pharmaceutically-useful agents to include one or more chiral centres. The complex structure of such compounds means that their synthesis involves many steps, and consequently where chiral centres are present, the compounds are usually prepared in the form of racemic mixtures.

The pharmacological activity of the compound is often mediated by the binding of the pharmacological agent to a target site. The more accurate the 3-dimensional fit between the pharmacological agent and the target site, the more potent the pharmacological activity, and the lower the likelihood of unwanted side-effects.

As a consequence of this, it is not unexpected that individual enantiomeric forms of a chiral compound show different pharmacological activity, differences in metabolic behaviour and different spectra of undesirable side-effects.

It is therefore desirable to ensure where possible that the end-products of synthesis of pharmaceutical compounds are enantiomerically pure.

Physicochemical methods for production of enantiomerically pure compounds usually involve multi-step synthesis incorporating one or more steps which are asymmetric, and laborious purification procedures. Such methods are not only tedious, but frequently provide relatively poor yields. Alternatively enantiomerically-pure starting materials can be used, together with enantioselective reaction steps; however, such pure starting materials are available only for a very limited number of desired compounds.

In recent years, efforts have been directed towards development of methods which are highly selective, provide a good rate of transformation, and enable easy, non-chromatographic separation and purification of the product. It has also been considered particularly desirable for the reactions to be carried out in non-aqueous solvents, since these are particularly convenient for large-scale reactions and purifications. In addition, where enantiomerically-pure reaction products cannot be obtained, changes in the physical environment in which the reactions are conducted can lead to improvements in the overall efficiency of the reaction system.

Some principle candidate classes of pharmaceutical compounds containing chiral centres which may be advantageously stereospecifically synthesized include aryl ethylamines such as ephedrine and the other sympathomimetic amines, aryl propylamines such as fluoxetine (Prozac) and the other serotonin selective uptake inhibitors, and propionic acid derivatives such as ibuprofen, naproxen and fenoprofen.

Ephedrine (α-[1-(methylamino)ethyl]benzene-methanol), originally isolated from plants of the genus Ephedra, occurs as the naturally occurring isomers l-ephedrine and d-pseudoephedrine, and other pharmacologically active isomers include d-ephedrine and l-pseudoephedrine. These compounds are adrenergic sympathomimetic agents and have antihistamine activity; l-ephedrine is widely used as a bronchodilator, while d-pseudoephedrine is widely used as a decongestant. Compounds of these groups are present in a very wide range of prescription and over-the-counter pharmaceutical formulations.

The production of l-phenylacetylcarbinol (PAC), a precursor of l-ephedrine, by catalysis using whole baker's yeast cells in aqueous medium was one of the first microbial biotransformation processes to be used commercially. This reaction included the yeast-mediated reduction of a ketone intermediate to produce the chiral phenylacetylcarbinol, although today the more common synthetic route involves yeast-mediated condensation between benzaldehyde and pyruvate to form PAC.

The yeast-catalysed systems have utilised aqueous solvent systems, which have been found to be inconvenient for large-scale extraction and purification. Additional problems associated with the aqueous solvent systems are the low yields and low purity. Whilst the reaction has been improved by utilising immobilised cells, or cells which have been selected or genetically modified, this adds significantly to the cost of the process. The use of purified enzymes is normally prohibitively expensive, and again without the use of immobilised enzymes the yields tend to be low and purification difficult. In view of the difficulty of large-scale extraction and purification with the aqueous solvent systems, organic systems, supercritical fluid systems and liquefied gas systems have been investigated.

In our earlier International Application PCT/AU00/01543, we showed that yeast-mediated acyloin condensation of benzaldehyde could be achieved in supercritical or liquefied carbon dioxide or in liquefied petroleum gas. The use of supercritical fluids as the reaction medium in large scale reactions is advantageous as compared with conventional organic solvents since the purification and processing of the products is simpler. However, the use of such reagents requires specialised equipment design and control that add to expense.

There is accordingly still room for the current systems for synthesising pharmaceutical compounds to be improved upon.

It has now been surprisingly found by the present applicant that yeast mediated reduction reactions of organic compounds can be conducted in the absence of a solvent. The present applicant has established that a broad range of important pharmaceutical compounds containing chiral centres can be synthesized using a route in which a starting compound is subjected to a yeast-mediated reduction reaction to provide a product, which may be enantiomerically pure, and which can then be converted into one isomer of the target pharmaceutical compound. In cases where the product is a racemic mixture, the process provides improvements in process efficiencies, such as the simple isolation of a product without a liquid-liquid separation step.

SUMMARY OF THE INVENTION

According to one aspect of the present invention there is provided a method of reducing an organic compound, comprising subjecting the organic compound to a yeast mediated reduction wherein the reduction is conducted in the absence of a solvent.

It will be understood to a person skilled in the art that the yeast mediated reaction requires some water for the reaction to take place. Sufficient water is required for enzymes to be hydrated and take the appropriate configuration. A "monolayer" of water around the enzymes is required. For many compounds, the presence of larger volumes of water (i.e.

sufficient water to provide a separate water layer) prevents or substantially prevents the yeast-mediated reduction of that compound from taking place. This is particularly the case for water-insoluble organic compounds. In contrast, the applicant has surprisingly found that these water-insoluble compounds react rapidly and with high yield when simply mixed with near-dry or damp yeast (i.e. yeast with insufficient water to provide a visible separate water layer). This level of water corresponds to a water-to-yeast ratio of up to 1.5 ml/g (approximately 60% w/w). The minimum amount of water required is approximately 0.2 ml/g of yeast (approximately 10% w/w). Dry yeast contains at most 1-3% w/w water, and therefore must be wetted to be activated for use according to the present invention. Preferably, the water to yeast ratio is 0.8 to 1.2 ml/g of yeast (approximately 44 to 55% w/w).

Whilst water is sometimes used as a solvent in organic reactions (particularly for reactions involving water-soluble organic reagents), according to the present invention water is not used in a high enough volume to function as a solvent. Accordingly, it is to be understood that the water is not a solvent in the context of the present application.

Any yeast capable of effecting the reduction reaction may be used. It is economically advantageous to use the cheapest yeast available, and ordinary baker's yeast, *Saccharomyces cerevisiae*, is preferred. Strains of yeast adapted to other purposes, including brewing yeast and wine or sherry yeasts could also be employed. For maximum efficiency of reaction, it is advisable to present the maximum surface area of yeast for contact with the reactants. This can be effected by using "active" dried yeast, which is readily commercially available as "instant dry yeast", and may be stored at room temperature. Alternatively, well-pulverised dry baker's yeast may be used. Typically "dry yeasts" have 1-3% w/w water. Other yeasts, such as those described in U.S. Pat. No. 4,734,367, or fungi such as those disclosed in Chênevert et al (1992) (Chênevert, R. Fortier, G. and Rhlid, R. B., Tetrahedron, 1992 48 6769-6776) may also be used. The person skilled in the art will readily be able to test whether any specific organism will function for the purposes of the invention, using the methods described herein.

The yeast mediated reduction reaction is significantly faster than prior art methods and also provides an improved result. The applicant has achieved greater than 80% isolated yield as a result of complete reduction of the organic compound. Little or no side products are produced. No side products have been detected in the products of the reaction by the present applicant.

The proportion of yeast to organic compound may be anything from 0.1 gram of yeast per mmol of organic compound, up to 50 grams of yeast per mmol of organic compound. However, the preferred range is about 0.8 to 20 g/mmol. While it is possible to speed up the reaction by the use of extra yeast, this is usually unnecessary.

The reaction is carried out in non-fermenting conditions at temperatures between 0 to 50° C. For optimum results, the reaction is carried out at room temperature. Usually the reaction is conducted at atmospheric pressure, although it is noted that the reaction is not affected by changes in pressure.

Preferably, the method of the invention involves contacting the organic compound with the yeast and water to form a mixture, leaving the mixture for sufficient time for the reaction to take place, adding an organic solvent to the mixture to dissolve the product of the reaction into the organic solvent, and conducting a solid/liquid separation to separate the product of the reaction from the yeast. Preferably the solvent is evaporated to yield the product of the reaction.

The water that is present in the mixture is present in such a small amount that it "sticks" to the yeast, and does not interfere with the removal of the product of the reaction (an organic compound) into the organic solvent. It is a significant advantage of the method of the invention that a biphasic (aqueous/organic) extraction is avoided. Biphasic extractions are often associated with low isolated yields. It is also an advantage of the invention that no reagents (in this case, the water/yeast) are extracted into the organic solvent, so that no separate purification steps are required.

A broad range of organic compounds can be reduced using the method of the present invention. Specific classes of compounds that may be reduced by the reaction include ketones, alkenes, alkynes, aldehydes, imines (i.e. compounds containing the group —C=N—) and hydroxamines.

The reaction is most effective on conjugated or activated ketones and alkenes.

Consequently, particularly suitable classes of organic compounds for subjecting to the method of the present invention are β-keto amides, β-keto esters, enol ethers, activated ketones and conjugated (activated) alkenes (i.e. alkenes with an atom with an electrophilic character, as may be provided, for example by alkenes substituted with $NO_2$, —CN, ketone, ester, amide, aldehyde, thioether, alkene, aromatic groups, halogens, etc).

Amongst these organic compounds, some classes are industrially very useful precursors in the synthesis of known pharmaceutical agents. Particularly suitable classes of organic compounds which may be reacted according to the method of the invention to form useful precursor compounds include the following:

Activated ketones (I), (II), and (III):

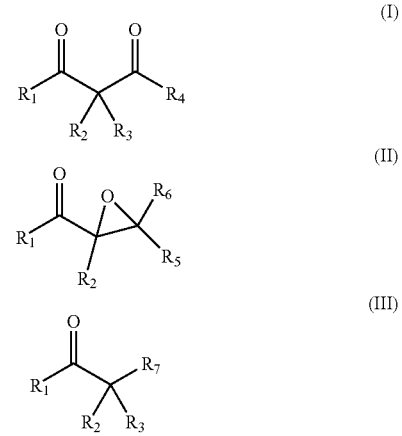

in which:

$R_1$ is an optionally substituted aryl group;

$R_2$, $R_3$, $R_5$ and $R_6$ are H or optionally substituted $C_1$-$C_6$ alkyl;

$R_4$ is an optionally substituted $C_1$-$C_6$ alkoxy, aryloxy, amino, optionally substituted di-($C_1$-$C_6$alkyl) amino, optionally substituted alkarylamino optionally substituted $C_1$-$C_6$ alkylamino, optionally substituted cyclic amino, such as pyrrolidino, piperidino, imidazolidinyl, piperazinyl, morpholinyl, $C_{1-6}$alkylpyrrolidino or $C_{1-6}$alkylpiperidino; and $R_7$ is cyano; nitro; halo; OH; $NH_2$; $C_{1-6}$ alkyl substituted by OH, halo, amine, or $C_{1-6}$ alkylamino;

Conjugated Alkenes:

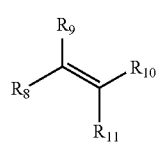

(IV)

wherein:

$R_8$ is an optionally substituted aromatic group;

$R_9$, $R_{10}$ and $R_{11}$ are each independently selected from H, hydroxy, $C_{1-6}$alkoxy, mercapto, $C_{1-6}$ alkylthio, amino, $C_{1-6}$alkylamino, di($C_{1-6}$alkyl)amino, carboxy, $C_{1-6}$alkoxycarbonyl, $C_{1-6}$aryloxycarbonyl, carbamoyl, $C_{1-6}$alkylcarbamoyl, di-$C_{1-6}$alkylcarbamoyl, $C_{1-6}$cycloalkylcarbamoyl, $C_{1-6}$alkylsulphonyl, arylsulphonyl, $C_{1-6}$alkylaminosulphonyl, di($C_{1-6}$alkyl)aminosulphonyl, nitro, cyano, cyano-$C_{1-6}$alkyl, hydroxy$C_{1-6}$alkyl, amino-$C_{1-6}$alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, halo, halo$C_{1-6}$alkyl, or halo$C_{1-6}$alkoxy, alkoximino, hydroximino, and alkylimino.

To generate a new chiral centre, one of $R_9$, $R_{10}$ and $R_{11}$ must not be H. Accordingly, preferably at least one of $R_9$, $R_{10}$ and $R_{11}$ is not H.

For the compounds of Formulae (I), (II) and (III), $R_1$ is preferably substituted or unsubstituted phenyl or 2-thienyl. The phenyl group may contain one or more substituents, preferably selected from hydroxy, methyl, methoxy, hydroxymethyl and trifluoromethyl.

For the compounds of Formulae (I), (II) and (III), $R_2$ is preferably H, and $R_3$ is preferably either H, methyl or ethyl. Most preferably $R_3$ is also H.

$R_4$ in the compound of Formula (I) is preferably methoxy, ethoxy, $C_{1-6}$ alkylamino, $NH_2$, or di($C_1$-$C_6$alkyl)amino. More preferably $R_4$ is $NH_2$ or $C_{1-6}$ alkylamino.

$R_5$ and $R_6$ in the compound of Formula (II) are preferably each H.

In the situation where the compound is of Formula (III), preferably $R_7$ is cyano, alkylhalo or $C_{1-6}$ alkylamino.

These compounds of Formula (I), (II) and (III) may be subjected to the method of the present invention to form precursors for the synthesis of seretonin selective uptake inhibitors and related compounds such as fluoxetine (Prozac), tomoxetine, duloxetine, nisoxetine, and each of the compounds defined in U.S. Pat. No. 4,314,081, as well as epinephrine, norepinephrine, ethylnorepinephrine, isoproterenol, isoetharine, metaproterenol, terbytaline, metaproterenol, phenylephrine, ritodrine, prenalterol, methoxamine, albuterol and derivatives with N-substitution such as salmeterol, ephedrine, phenylpropanolamine. The routes to the synthesis of these compounds from the compounds of Formulae (I), (II) and (III) are described in further detail below.

The compound of Formula (IV) may be used as the starting compound for the synthesis of the pharmaceuticals listed above, together with amphetamine and its derivatives such as hydroxyamphetamine, methamphetamine, benzphetamine, fenfluramine, propylhexedrine, and propionic acid derivatives, such as ibuprofen, naproxen, alminoprofen, fenoprofen, flurbiprofen, indoprofen, ketoprofen and suprofen.

For the compounds of Formula (IV), the aromatic group $R_8$ may be substituted or unsubstituted phenyl when the compound is to be used for the synthesis of the sympathomimetic amines and phenylpropylamines such as Prozac. The preferred substituents on the phenyl group are hydroxy, methyl, methoxy, hydroxymethyl and trifluoromethyl. For the synthesis of the propionic acid derivatives referred to above from the compound of Formula (IV), the aryl group may be substituted phenyl (such as p-isobutyl for ibuprofen, 3-phenoxyphenyl for fenoprofen, 2-fluoro-4-biphenyl for flurbiprofen, 4-(1,3-dihydro-1-oxo-2H-isoindol-2-yl)phenyl, 3-benzoylphenyl for ketoprofen, p-(2-thenoyl)phenyl for suprofen or p-methylallylaminophenyl for alminoprofen) or a substituted napthyl (such as 6-methoxy2-napthyl- for naproxen). Consequently, the substituents on the phenyl and napthyl groups may be selected from a wide variety of substituents.

For the preparation of propionic acid derivatives, $R_{10}$ and $R_{11}$ are preferably each H, and $R_9$ is carboxy or $C_{1-6}$alkoxycarbonyl.

For the preparation of one of the more commonly used ethylamines containing a substituent on the α-carbon atom (such as amphetamine) from compound (IV), preferably $R_9$ is H or hydroxy. Preferably, one of $R_{10}$ and $R_{11}$ is selected from $C_{1-6}$alkyl, and more preferably methyl or ethyl. Preferably the other of $R_{10}$ and $R_{11}$ is selected from $C_{1-6}$alkoxycarbonyl, $C_{1-6}$aryloxycarbonyl, carbamoyl, $C_{1-6}$alkylcarbamoyl, di-$C_{1-6}$ alkylcarbamoyl, $C_{1-6}$cycloalkylcarbamoyl or nitro.

For the preparation of one of the more commonly used propylamines containing a substituent on the β-carbon atom (such as fluoxetine) from compound (IV), preferably $R_9$ is hydroxy. More preferably, one of $R_{10}$ and $R_{11}$ is selected from H and $C_{1-6}$alkyl, and more preferably it is H. Preferably the other of $R_{10}$ and $R_{11}$ is selected from cyano, $C_{1-6}$alkoxycarbonyl, $C_{1-6}$aryloxycarbonyl, carbamoyl, $C_{1-6}$alkylcarbamoyl, di-$C_{1-6}$alkylcarbamoyl and $C_{1-6}$cycloalkylcarbamoyl.

According to the present invention, there is also provided a method of synthesising a pharmaceutical compound comprising the step of subjecting a precursor to a yeast mediated reduction wherein the reduction is conducted in the absence of a solvent; and converting the product of the reduction reaction into the pharmaceutical compound.

Preferably, the pharmaceutical compound is a sympathomimetic amine, an ethyl amine, a propylamine or a propionic acid. More preferably, the pharmaceutical compound is an arylethylamine, an arylpropylamine, or a propionic acid with a 2-aryl substitution.

Particular pharmaceutical compounds that can be synthesized via the solvent-free yeast mediated reduction step of the present invention are fluoxetine (Prozac), tomoxetine, duloxetine, nisoxetine, epinephrine, norepinephrine, ethylnorepinephrine, isoproterenol, isoetharine, metaproterenol, terbytaline, metaproterenol, phenylephrine, ritodrine, prenalterol, methoxamine, albuterol and derivatives with N-substitution such as salmeterol, derivatives of amphetamine, ephedrine, phenylpropanolamine, amphetamine and its derivatives such as hydroxyamphetamine, methamphetamine, benzphetamine, fenfluramine and propylhexedrine, ibuprofen, naproxen, alminoprofen, fenoprofen, flurbiprofen, indoprofen, ketoprofen and suprofen.

DETAILED DESCRIPTION OF THE PREFERRED EMBODIMENTS

A number of chemical terms used in the above description of the invention are defined below to avoid any ambiguity.

The term "alkyl" used either alone or in a compound word such as "optionally substituted alkyl" or "optionally substituted alkylamino" denotes straight chain, branched or mono- or poly-cyclic alkyl, preferably $C_{1-6}$ alkyl or cycloalkyl. Examples of straight chain and branched $C_{1-6}$ alkyl include methyl, ethyl, propyl, isopropyl, butyl, isbutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl and 1,1,2-trimethylpropyl.

The term "aryl" used either alone or in compound words such as "optionally substituted aryl", "optionally substituted aryloxy" or "optionally substituted heteroaryl" denotes single, polynuclear, conjugated and fused residues of aromatic hydrocarbons or aromatic heterocyclic ring systems. Examples of aryl include phenyl, biphenyl, terphenyl, quaterphenyl, phenoxyphenyl, naphtyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, pyrrolyl, furanyl, imadazolyl, pyrrolydinyl, pyridinyl, piperidinyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferably, the aromatic heterocyclic ring system contains 1 to 4 heteroatoms independently selected from N, O and S and containing up to 9 carbon atoms in the ring.

In the description provided above, reference is made to optional substituents. In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, cyano, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, phosphorus-containing groups, azo, imino, nitrile, carboxylate and the like. Preferably the substituents are selected from $C_{1-6}$ alkyl, halo, trifluoromethyl, hydroxy, and $C_{1-6}$alkoxy.

EXAMPLES

The following reaction schemes are provided to illustrate how the method of the present invention can be incorporated into a reaction scheme for the stereoselective synthesis of a target pharmaceutical compound. The specific compounds referred to above have similar structures with different substituents, and methods for their synthesis are well known. The known synthetic methods can me modified to incorporate the new solvent-free yeast mediated stereoselective reduction step of the present invention in one of the following ways.

1. Preparation of Prozac (as One Example) from β-keto Esters or Amides.

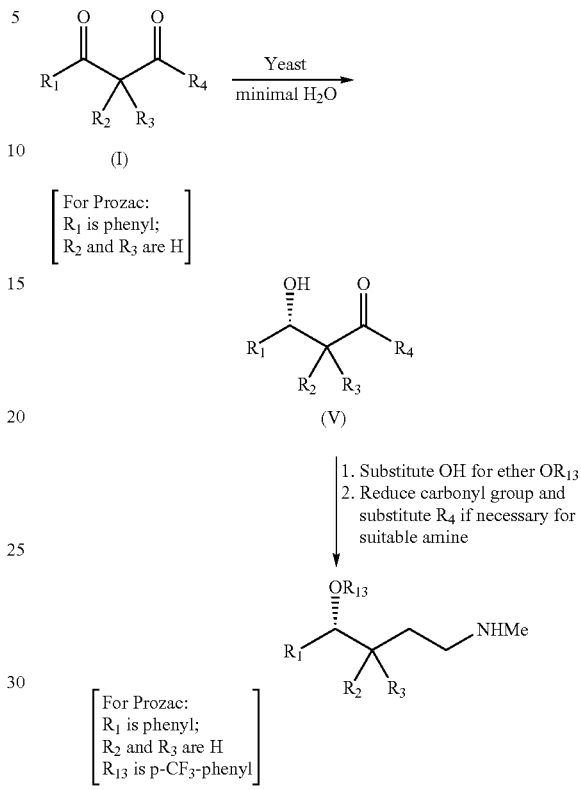

The above reaction scheme illustrates the synthesis of Prozac from a β-keto ester or amide, in accordance with the present invention. Suitable reagents and reaction conditions for conducting the steps following the yeast mediated reduction are outlined in *J. Org. Chem* 53 (17) 4081, particularly for the situation where $R_4$ is —$CH_2OH$.

Other propylamines can be synthesized using this technique by using the appropriate reagents. Table 1 details suitable target propylamines.

TABLE 1

| nd | $R_1$ | $R_2$ | $R_3$ |
|---|---|---|---|
| Fluoxetine (structure with CF3, O, Ph, NHMe) | Ph | H | H |
| Tomoxetine (structure with Me, O, Ph, NHMe) | Ph | H | H |

TABLE 1-continued

| nd | R₁ | R₂ | R₃ |
|---|---|---|---|
| Duloxetine | 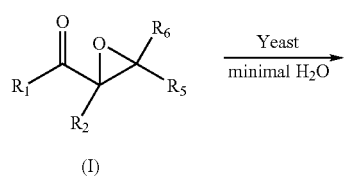 | (thiophene) | |
| Nisoxetine | | H | H |

2. Preparation of Prozac from β-keto Epoxide:

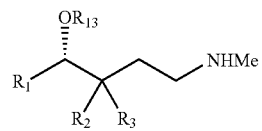

(I)

[For Prozac:
R₁ is phenyl;
R₂ and R₃ and H]

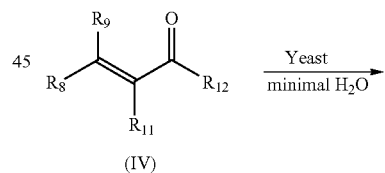

(VI)

1. Substitute OH for ether OR₁₃
2. Reduce epoxide and, if necessary, replace R₅ and/or R₆ with suitable amine.

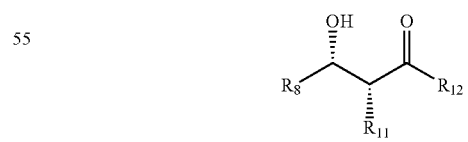

[For Prozac:
R₁ is phenyl;
R₂ and R₃ are H
R₁₃ is p-CF₃-phenyl]

Similarly to method 1 outlined above, this method can be applied to the synthesis of the compounds outlined in Table 2. See *J. Org. Chem.* 53(17) 4081.

TABLE 2

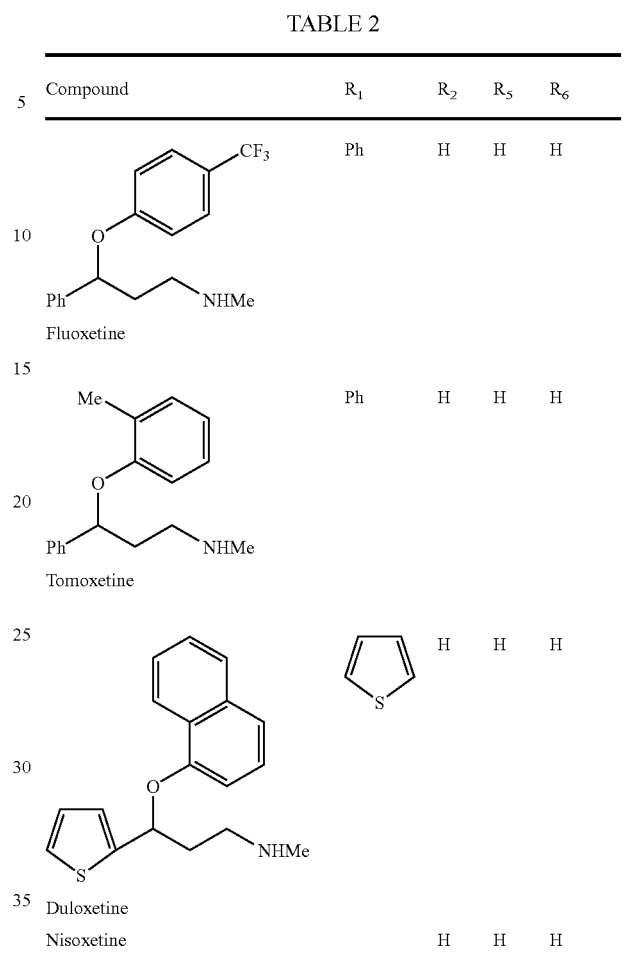

3. Preparation of Prozac from Enol Ether of β-keto Ester

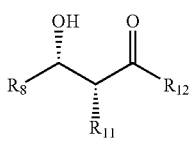

(IV)

$R_{12}$ is $O-C_{1-6}$alkyl, $N-di-C_{1-6}$ alkyl or N-cycloalkyl
(ie $R_{10}$ is $C_{1-6}$ alkoxycarbonyl, di-$C_{1-6}$alkycarbamoyl or $C_{1-6}$cycloalkylcarbamoyl.)

(VII)

1. Substitute OH for ether group
2. Reduce carbonyl group and substitute R₁₂ if necessary for suitable amine;

-continued

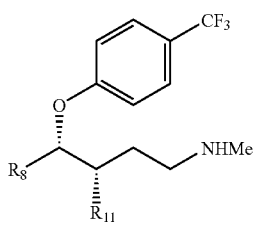

Again, aside from the yeast-mediated reduction step, appropriate reaction reagents and conditions are set out in *J. Org. Chem.* 53(17) 4081. The yeast-mediated reduction is conducted in accordance with the procedure outlined in the Experimental section.

This procedure can also be used for the synthesis of the compounds outlined in Table 3.

TABLE 3

| Compound | | $R_8$ | $R_2$ | $R_{11}$ |
|---|---|---|---|---|
| Fluoxetine | 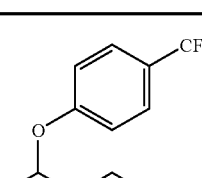 | Ph | H | H |
| | 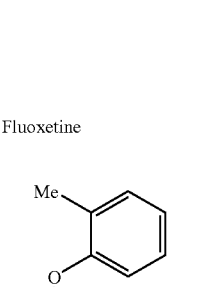 | Ph | H | H |

TABLE 3-continued

| Compound | | $R_8$ | $R_2$ | $R_{11}$ |
|---|---|---|---|---|
| Tomoxetine | | | H | H |
| Duloxetine | 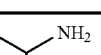 | | | |
| Nisoxetine | | | H | H |

4. Preparation of Amphetamine from Conjugated Alkene:

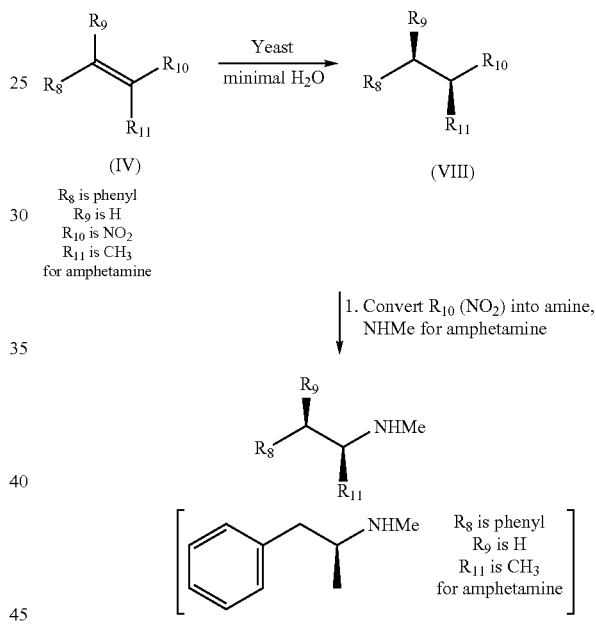

$R_8$ is phenyl
$R_9$ is H
$R_{10}$ is $NO_2$
$R_{11}$ is $CH_3$
for amphetamine 1. Convert $R_{10}$ ($NO_2$) into amine, NHMe for amphetamine $R_8$ is phenyl
$R_9$ is H
$R_{11}$ is $CH_3$
for amphetamine The procedure outlined above can likewise be utilised for the synthesis of the compounds outlined in the Table 4.

TABLE 4

| Compound | | $R_8$ | $R_9$ | $R_{10}$ | $R_{11}$ |
|---|---|---|---|---|---|
| Amphetamine |  | Ph | H | $NO_2$ | $CH_3$ |
| Epinephrine |  | | OR | $NO_2$ | H |

TABLE 4-continued
| Compound | R8 | R9 | R10 | R11 |
|---|---|---|---|---|
| 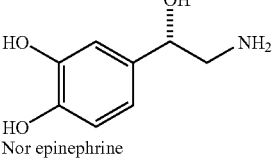 Nor epinephrine | 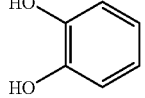 | OR | NO2 | H |
| 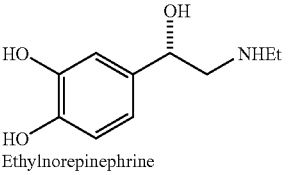 Ethylnorepinephrine | 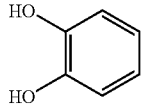 | OR | NO2 | H |
| 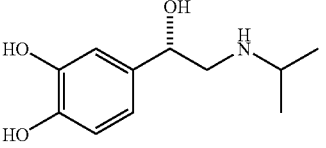 Isoproterenol | 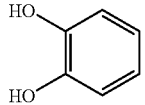 | OR | NO2 | H |
| 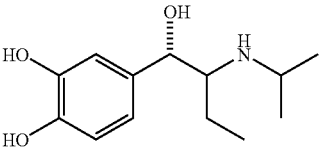 Isoetharine | 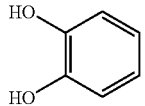 | OR | NO2 | $CH_2CH_3$ |
| 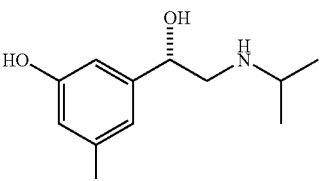 Metaproterenol | 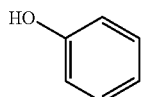 | OR | NO2 | H |
| 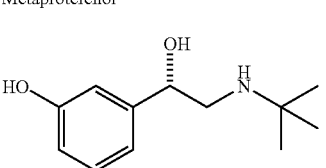 Terbutaline | 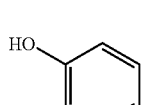 | OR | NO2 | H |
| 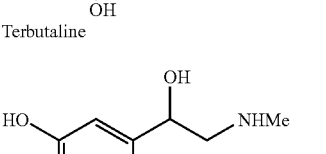 Phenylephrine | 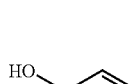 | OR | NO2 | H |
| 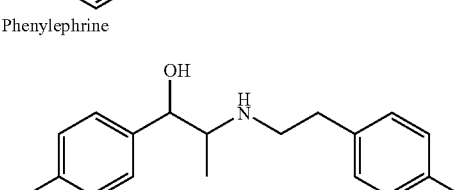 Ritodrine | 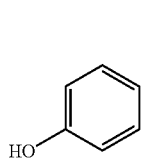 | OR | NO2 | $CH_3$ |

TABLE 4-continued

| Compound | | R₈ | R₉ | R₁₀ | R₁₁ |
|---|---|---|---|---|---|
| Prenalterol | (4-hydroxyphenoxy-CH₂-CH(OH)-CH₂-NH-iPr) | 4-methoxyphenol | OR | NO₂ | H |
| Methoxamine | (2,5-dimethoxyphenyl-CH(OH)-CH(NH₂)-CH₃) | 2,5-dimethoxyphenyl | OR | NO₂ | CH₃ |
| Albuterol | (3-hydroxymethyl-4-hydroxyphenyl-CH(OH)-CH₂-NH-tBu) | 2-hydroxymethylphenol | OR | NO₂ | H |
| Salmeterol | (3-hydroxymethyl-4-hydroxyphenyl-CH(OH)-CH₂-NH-(CH₂)₆-O-(CH₂)₄-Ph) | 2-hydroxymethylphenol | OR | NO₂ | H |
| Ephedrine | (Ph-CH(OH)-CH(NHMe)-CH₃) | Ph | OR | NO₂ | CH₃ |
| Phenylpropanolamine | (Ph-CH(OH)-CH(NH₂)-CH₃) | Ph | OR | NO₂ | CH₃ |
| Hydroxyamphetamine | (4-hydroxyphenyl-CH₂-CH(NHMe)-CH₃) | phenol | H | NO₂ | CH₃ |
| Methamphetamine | (Ph-CH₂-CH(NHMe)-CH₃) | Ph | H | NO₂ | CH₃ |

TABLE 4-continued

| Compound | | $R_8$ | $R_9$ | $R_{10}$ | $R_{11}$ |
|---|---|---|---|---|---|
| Benzphetamine | 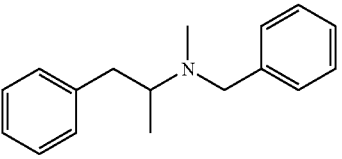 | Ph | H | $NO_2$ | $CH_3$ |
| Fenfluramine | 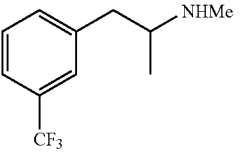 | 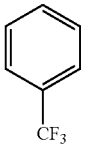 | H | $NO_2$ | $CH_3$ |
| Propylhexedrine | 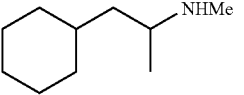 |  | H | $NO_2$ | $CH_3$ |

5. Preparation of Ibuprofen

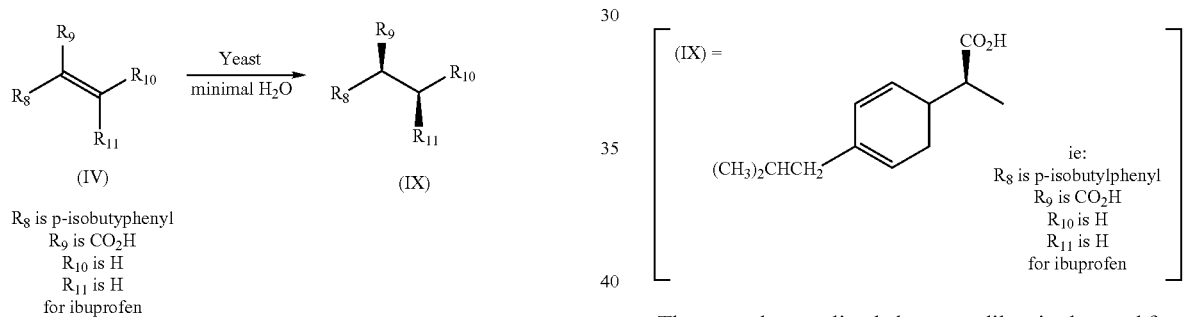

$R_8$ is p-isobutyphenyl
$R_9$ is $CO_2H$
$R_{10}$ is H
$R_{11}$ is H
for ibuprofen ie:
$R_8$ is p-isobutylphenyl
$R_9$ is $CO_2H$
$R_{10}$ is H
$R_{11}$ is H
for ibuprofen The procedure outlined above can likewise be used for the synthesis of the compounds outlined in Table 5.

TABLE 5

| Compound | | $R_8$ | $R_9$ | $R_{10}$ | $R_{11}$ |
|---|---|---|---|---|---|
| Ibuprofen | 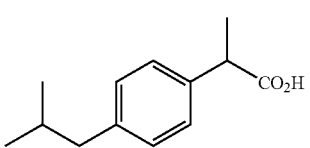 | 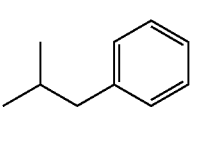 | COOH | H | H |
| Naproxen | 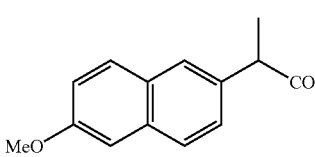 | 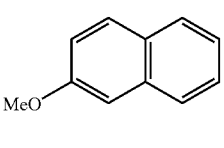 | COOH | H | H |

TABLE 5-continued

| Compound | R8 | | R9 | R10 | R11 |
|---|---|---|---|---|---|
| Alminoprofen | (structure) | (structure) | COOH | H | H |
| Fenoprofen | (structure) | (structure) | COOH | H | H |
| Flurbiprofen | (structure) | (structure) | COOH | H | H |
| Indoprofen | (structure) | (structure) | COOH | H | H |
| Ketoprofen | (structure) | (structure) | COOH | H | H |
| Suprofen | (structure) | (structure) | COOH | H | H |

Experimental Procedure:

The present invention will now be described in further detail with reference to the following Examples.

1. Preparation of Ethyl (R)-3-hydroxy-3-phenylpropanoate (Method I).

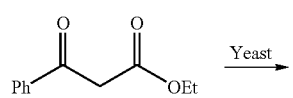

Yeast
→

-continued

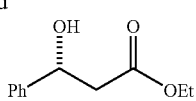

Ethyl benzoyl acetate (192 mg, 1 mmol) was added to water (10 mL, 1 mL/g yeast) in a 70 mL Pyrex test tube and vortexed until an even dispersion of substrate throughout the water was achieved (opaque mixture persists). Yeast (10 g/mmol) was then added quickly and vortex was maintained for a further 5 minutes. This procedure produced a moist pliable yeast that firmed up a few minutes after water had been incorporated into the yeast. The reaction was left at room temperature for 24 hours. The product was extracted from the yeast using ethyl acetate (2×30 mL). Evaporation under reduced pressure produced an essentially pure ethyl (R)-3-hydroxy-3-phenylbutanoate as an oil which can be further purified by distillation if necessary (isolated yield 86%) This reaction was repeated several times and achieved similar yields.

2. Preparation of Ethyl (R)-3-hydroxy-3-phenylpropanoate (Method II)

Ethyl benzoyl acetate (192 mg, 1 mmol) was added to diethylether (10 mL) and the solution applied to a sheet of filter paper. The solvent was left to evaporate. Yeast (10 g/mmol) was mixed with water (10 ml) and the resultant paste spread onto the filter paper and left for 24 h. The product was extracted from the yeast using ethyl acetate (2×30 mL). Evaporation under reduced pressure produced an essentially pure ethyl (R)-3-hydroxy-3-phenylbutanoate as an oil.

3. Preparation of Ethyl (S)-3-hydroxybutanoate

Ethyl acetoacetate (130 mg, 1 mmol) was reacted with yeast (2 g) and water (2 ml) according to method I. Extraction of the yeast gave the pure product in 80% yield. The reaction was repeated following the general procedure of Method II outlined above to yield a pure product in 78% yield.

4. Preparation of 2-nitro-3-phenylpropane

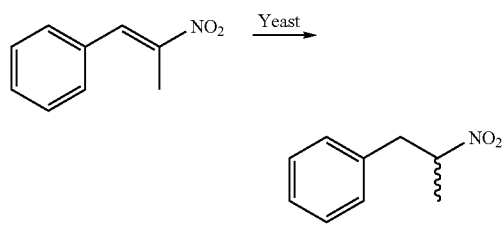

Z-2-nitro-3-phenyl-2-propene (151 mg 1 mmol) was reacted with yeast (5 g) and water (5 ml) according to Method I. The product was isolated as a racemic mixture of products in 41% yield. Reaction according to method II also resulted in a racemic mixture of products in 38% yield.

5. Preparation of Ethyl (R)-3-methoxy-3-phenylpropanoate

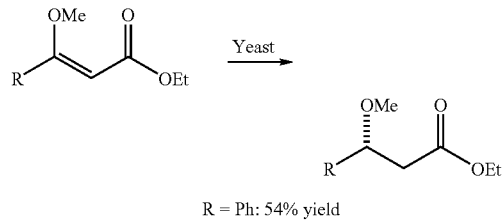

R = Ph: 54% yield

Ethyl 3-methoxy-3-phenylpropenoate (206 mg, 1 mmol) was reacted with yeast (10 g) and water (10 ml) according to method I. The product was obtained in 54% yield. Reaction according to method II gave the product in 60% yield.

6. Preparation of Ethyl (S)-3-methoxybutanoate

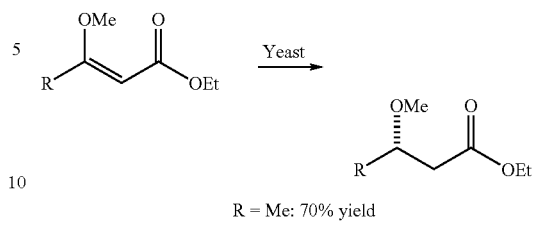

R = Me: 70% yield

Ethyl 3-methoxy-2-butenoate (144 mg, 1 mmol) was reacted according to Method I. The product was obtained in 70% yield. Reaction according to method II gave the product in 70% yield.

7. Preparation of 2-phenylethanol

Acetophenone (120 mg, 1 mmol) was reacted with yeast (5 g) and water (5 ml) according to method I. The product was obtained in 50% yield. Reaction according to Method II gave the product in 52% yield.

Unlike a solvent based yeast mediated reduction reaction, there is no interference in the isolation process from extracted biomass material product and therefore chromatographic purification is not needed to obtain pure product; and unlike an aqueous based yeast mediated reduction reaction system, biphasic extractions, often associated with low isolated yields, are avoided.

The steps required to synthesise the range of pharmaceutical compounds from the precursors described in this application are will within the skill and knowledge of the person in the art of the invention.

The foregoing Examples are provided for illustration of the concept of the invention only. Modifications may be made to the preferred embodiments without departing from the spirit and scope of the invention.

The invention claimed is:

1. A method of reducing an organic compound of Formula IV:

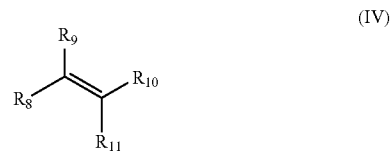

wherein:
$R_8$ is an optionally substituted aromatic group;
$R_9$, $R_{10}$ and $R_{11}$ are each independently selected from H, hydroxy, $C_{1-6}$alkoxy, mercapto, $C_{1-6}$ alkylthio, amino, $C_{1-6}$alkylamino, di($C_{1-6}$alkyl)amino, carboxy, $C_{1-6}$alkoxycarbonyl, $C_{1-6}$aryloxycarbonyl, carbamoyl, $C_{1-6}$alkylcarbamoyl, di-$C_{1-6}$alkylcarbamoyl, $C_{1-6}$cycloalkylcarbamoyl, $C_{1-6}$alkylsulphonyl, arylsulphonyl, $C_{1-6}$alkylaminosulphonyl, di($C_{1-6}$alkyl)aminosulphonyl, nitro, cyano, cyano-$C_{1-6}$alkyl, hydroxy$C_{1-6}$alkyl, amino-$C_{1-6}$alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, halo, halo$C_{1-6}$alkyl, or halo$C_{1-6}$alkoxy, alkoximino, hydroximino, and alkylimino;
the method comprising subjecting the organic compound to a yeast-water paste of a yeast mediated reduction in the presence of an amount of water that is sufficient for enzymes to be hydrated and but insufficient to provide a visibly separate water layer wherein the reduction is conducted in the absence of any additional solvents, and wherein a water-to-yeast ratio is up to 1.5 ml/g.

2. The method of claim 1, wherein the water-to-yeast ratio is between 0.2 ml/g and 1.5 ml/g.

3. The method of claim 2, wherein the water-to-yeast ratio is between 0.8 and 1.2 ml/g of yeast.

4. The method of claim 1, wherein the reduction is conducted in the presence of water in an amount of 44 to 55% w/w based on the weight of yeast.

5. The method of claim 1, wherein the proportion of yeast to organic compound is from 0.1 gram of yeast per mmol of organic compound, up to 50 grams of yeast per mmol of organic compound.

6. The method of claim 5, wherein the proportion of yeast to organic compound is 0.8 to 20 g/mmol.

7. The method of claim 1, wherein the reaction is carried out in non-fermenting conditions at temperatures between 0 to 50° C.

8. The method of claims 1, wherein the reaction is carried out at room temperature.

9. The method of claim 1, wherein the reaction is conducted at atmospheric pressure.

10. The method of claim 1, wherein the method comprises the steps of contacting the organic compound with the yeast and water in the absence of any additional solvents to form a mixture, leaving the mixture for sufficient time for the reaction to take place, adding an organic solvent to the mixture to dissolve a product of the reaction into the organic solvent, and conducting a solid/liquid separation to separate the product of the reaction from the yeast.

11. The method of claim 10, further comprising evaporating the solvent to isolate the product of the reaction.

12. The method of claim 1, wherein one of $R_9$, $R_{10}$ and $R_{11}$ is not H.

13. The method of claim 1, the group $R_8$ is selected from the group consisting of phenyl, substituted phenyl, napthyl and substituted napthyl.

14. The method of claim 1, wherein $R_{10}$ and $R_{11}$ are each H, and $R_9$ is carboxy or $C_{1-6}$alkoxycarbonyl.

15. The method of claim 1, wherein $R_9$ is H or hydroxy, one of $R_{10}$ and $R_{11}$ is selected from $C_{1-6}$alkyl, and the other of $R_{10}$ and $R_{11}$ is selected from the group consisting of $C_{1-6}$alkoxycarbonyl, $C_{1-6}$aryloxycarbonyl, carbamoyl, $C_{1-6}$alkylcarbamoyl, di-$C_{1-6}$alkylcarbamoyl, $C_{1-6}$cycloalkylcarbamoyl and nitro.

16. The method of claim 1, wherein $R_9$ is hydroxy, one of $R_{10}$ and $R_{11}$ is selected from H and $C_{1-6}$alkyl, and the other of $R_{10}$ and $R_{11}$ is selected from the group consisting of cyano, $C_{1-6}$alkoxycarbonyl, $C_{1-6}$aryloxycarbonyl, carbamoyl, $C_{1-6}$alkylcarbamoyl, di-$C_{1-6}$alkylcarbamoyl, and $C_{1-6}$cycloalkylcarbamoyl.

17. The method of claim 1, wherein the compound of Formula (IV) is a precursor for the synthesis of a pharmaceutical selected from the group consisting of fluoxetine, tomoxetine, duloxetine, nisoxetine, epinephrine, norepinephrine, ethylnorepinephrine, isoproterenol, isoetharine, metaproterenol, terbytaline, metaproterenol, phenylephrine, ritodrine, prenalterol, methoxamine, albuterol or a derivative thereof, salmeterol, ephedrine and phenylpropanolamine, amphetamine or a derivative thereof, hydroxyamphetamine, methamphetamine, benzphetamine, fenfluramine, propylhexedrine, ibuprofen, naproxen, alminoprofen, fenoprofen, flurbiprofen, indoprofen, ketoprofen and suprofen, the method further comprising the step of converting the precursor into the pharmaceutical.

18. The method of claim 1, wherein the organic compound and the yeast-water paste forms a moist pliable yeast.

19. The method of claim 1, wherein the method avoids biphasic extractions before the step of adding the organic solvent to the mixture.

20. The method of claim 1, wherein the yeast mediated reduction is carried out in non-fermenting conditions.

* * * * *